United States Patent
Hao et al.

(10) Patent No.: US 6,627,219 B2
(45) Date of Patent: Sep. 30, 2003

(54) OILY CAPSULE PREPARATION AND THE METHOD FOR PREPARING SAME

(75) Inventors: Wei-Hua Hao, Taipei (TW); Shih Min Chen, Taipei County (TW)

(73) Assignee: Pharmaceutical Industry Technology and Development Center (TW)

( * ) Notice: Subject to any disclaimer, the term of this patent is extended or adjusted under 35 U.S.C. 154(b) by 0 days.

(21) Appl. No.: 09/896,103

(22) Filed: Jun. 29, 2001

(65) Prior Publication Data

US 2002/0076435 A1 Jun. 20, 2002

(30) Foreign Application Priority Data

Jul. 1, 2000 (TW) ........................................ 89113073 A

(51) Int. Cl.[7] .............................. A61K 9/48; A61K 9/62; A61K 9/58
(52) U.S. Cl. ........................ 424/451; 424/452; 424/454; 424/461; 424/462; 424/463
(58) Field of Search ................................. 424/451, 452, 424/454, 461, 462, 463

(56) References Cited

U.S. PATENT DOCUMENTS 2,540,979 A    2/1951  Clymer et al.
6,306,435 B1 * 10/2001  Chen et al. ................. 424/457
6,428,810 B1 *  8/2002  Bergstrand et al. ......... 424/480

FOREIGN PATENT DOCUMENTS

JP          781102957         4/1978

OTHER PUBLICATIONS

Anders Karlsson; Pharmacy Practice; International Pharmacy Journal vol. 10, No. 6, pp. 210–213, 1996.

Scand J. Gastroenterol Development of an Oral Formulation of Omeprazole; 1985; 20 (Suppl 108): 113–120.

* cited by examiner

Primary Examiner—Carlos A. Azpuru
(74) Attorney, Agent, or Firm—LaRiviere Grubman Payne, LLP

(57) ABSTRACT

The present invention provides a oral capsule preparation, comprising a capsule prepared from a drug or the alkaline salt thereof, an oily compound or the alkaline salt thereof, an emulsifier and a polycarbon alcohol, together with an enteric coating disposed on the outer layer of the capsule; wherein said emulsifier is a composition of C6–18 organic fatty acid and an organic amine, or the mixture thereof. The invention also provides a method of preparing the oral capsule preparation of the invention.

42 Claims, 1 Drawing Sheet

OILY CAPSULE PREPARATION AND THE METHOD FOR PREPARING SAME

CROSS-REFERENCE TO RELATED APPLICATION(S)

This application claims priority from ROC Patent Application Serial Number 089113073 filed Jul. 1, 2000.

1. Technical Field

The present invention relates to a novel oral capsule preparation and the method for preparing the same.

2. Description of the Prior Art

For the drugs that are unstable, badly sensory or difficult to exhibit the efficacy, there are many problems in administration and manufacture. For example, those drugs are easily denatured, unable to fully exhibit the efficacy, or difficult to prepare. Therefore, it is necessary to develop a pharmaceutical formulation that can be easily produced with the improved bioavailability and enhanced stability.

In the prior art, for the drugs that are unstable, badly sensory or difficult to exhibit the efficacy, the powder modification or coating engineering process are need to provide the desired stability and curative effect when they are made as solid preparations. Therefore, the quality control of drugs is difficult due to different sources of raw materials or variation of the engineering techniques.

One aspect of the study in unstable drugs is anti-gastric ulcer drugs, wherein omeprazole is the most potent. According to the market survey and the evaluation of the developments of the drugs, the sale of omeprazole will stand the first in the world among the anti-gastric ulcer drugs.

Omeprazole ($C_{12}H_{19}N_3O_3S$), 5-methoxy-2(((4-methoxy-3,5-dimethyl-2-pyridinyl)methyl)sulfinyl)1H-benzimidazole, is an inhibitor of hydrogen potassium adenine nucleotidase, which is hardly soluble in water. Omeprazole is stable in the basic medium of a pH higher than 7 but is easily degraded or denatured in a neutral or acid medium (Pilbrant and Cederberg, Scand. J. Gastroenterology 1985; 20 (Supp. 108), pp. 113–120). For example, the half-life of omeprazole is only ten minutes in an aqueous solution at a pH less than 4 but is 14 hours in that solution at pH 7. Therefore, an oral dosage of omeprazole must be kept away from gastric juice to avoid the degradation before it reaches the small intestines.

Most omeprazole products are made from Astra Company. For example, ROC (Taiwan) Patent Application No. 76102439 provides an oral preparation of omeprazole, consisting of a core material (mixed with a basic compound or not) coated with one or more sublayer wherein the basic core contains omeprazole in combination with the buffered basic compound thereof such that the pH condition around omeprazole can be maintained in the range of 7–12. However, the cost is expensive because the process, time and control of the patented preparation are complicated.

ROC (Taiwan) Patent Application No. 78102957 discloses a solid pharmaceutical composition to increase the sustained time of omeprazole in stomach. However, there is no way to avoid a contact of omeprazole with gastric acid.

ROC (Taiwan) Patent Application No. 84104486 describes a process of preparing granulated preparations comprising the steps of: suspending omeprazole and an excipient in a suspension consisting of alcohol, water, ammonia water and binding agent; spraying the resulted suspension onto a core wherein the core is prepared from sugar, starch or microcrystal cellulose to obtain cored materials; adding the materials for granulation to the cored materials and then drying them. Omeprazole cannot be completely isolated from the acid environment during preparation such that the stability of omeprazole cannot be maintained well.

In the prior art, to prevent omeprazole from contacting with gastric juice, the omeprazole—containing cores are conventionally coated with enteric coatings. U.S. Pat. No. 2,540,979 provides an oral preparation with enteric coatings, wherein the enteric coatings are combined with a second and/or a first layer of water insoluble wax coating. However, a contact of omeprazole with acetate phthalate of the preparation reacts results in a degradation or color change of omeprazole.

Generally, an enteric coating is prepared from acid compounds. A direct or indirect contact of omeprazole with said acid compounds results in the denaturation and the loss of omeprazole. Karlsson, et. al. indicates that the stability of most omeprazole products, except Astra products is undesirable (Karlsson, et. al., 1996, International Pharmacy Journal, 10 (6); 210–213).

SUMMARY OF THE INVENTION

The invention provides an oral pharmaceutical preparation, which can be easily prepared, with an improved bioavailability and enhanced stability, which resolves the problems occurring in the prior art, such as unstability or difficulty in exhibiting the efficacy of omeprazole products.

One object of the invention is to provide an oral capsule preparation, which comprises a capsule prepared from a drug or the alkaline salt thereof, and oily compound or the alkaline salt thereof, an emulsifier, together with an enteric coating disposed on the capsule; wherein said emulsifier is a composition of $C_{6-18}$ organic fatty acid and an organic amine or a polycarbon alcohol or the mixture thereof.

Another object of the invention is to provide a method of preparing the oral capsule preparation of the invention, comprising the steps of suspending a drug or the basic salt thereof in an emulsified fluid formed by mixing oil compounds or the basic salts thereof and an emulsifier, filling a capsule with the suspension, coating the outer surface of the capsule with an enteric coating, wherein the emulsifier is a composition of $C_{6-18}$ organic fatty acid and an organic amine, or a polycarbon alcohol or the mixture thereof.

DETAILED DESCRIPTION OF THE INVENTION

Figure 1:
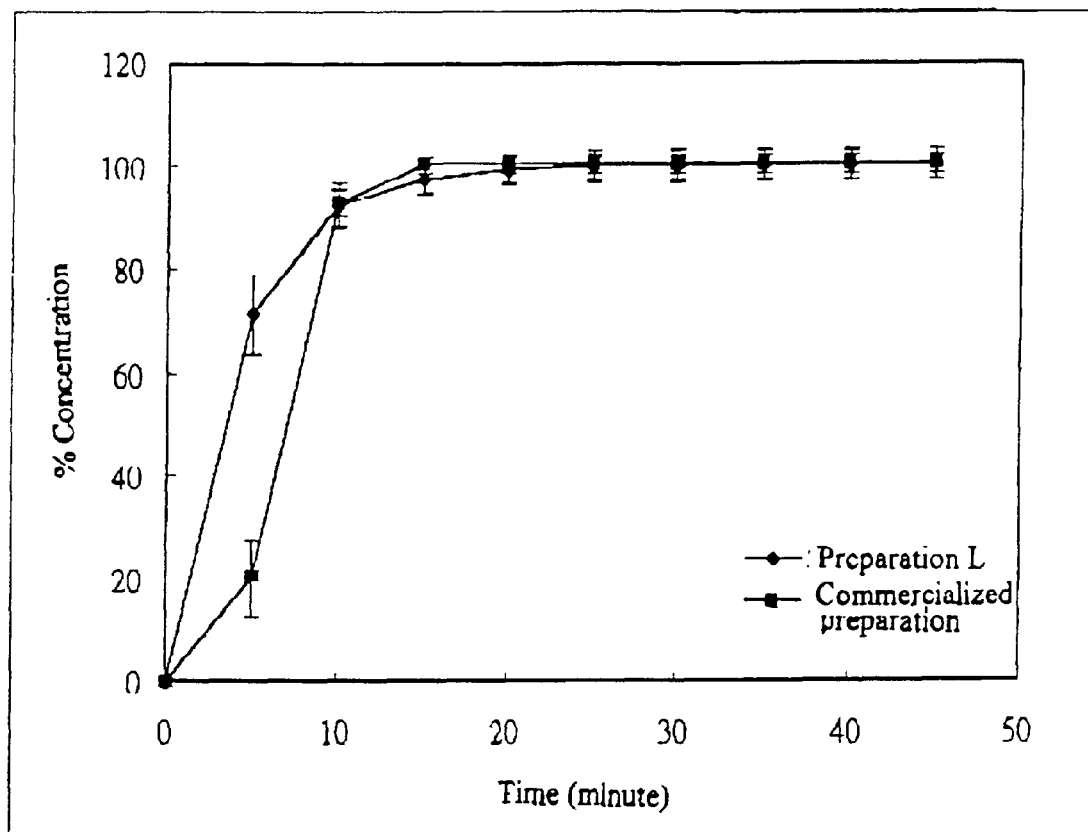
FIG. 1 is a plot of a comparative test illustrating the dissolution of the preparation L and conventional commercialized preparations containing omeprazole.

According to the invention, a pharmaceutical preparation technology that can apply to the preparation of the drugs which are unstable or difficult to exhibit the efficacy. The stability of the products according to the invention can be improved allow the drugs in a certain position to release and exhibit their best efficacy.

The invention provides an oral capsule preparation comprising a capsule prepared from a drug or the alkaline salt thereof, an oily compound or the alkaline salt thereof, an emulsifier, together with an enteric coating disposed on the capsule, wherein said emulsifier is a composition of $C_{6-18}$ organic fatty acid and an organic amine, or a polycarbon alcohol or the mixture thereof.

The term "drugs" as used herein refers to an active material with therapeutic efficacy. According to the invention, the drugs particularly refer to those drugs to be improved, such as those drugs that are unstable, badly sensory or difficult to exhibit the efficacy. Such drugs include the drugs containing the function groups of ester, amide, thiol ester, acid chloride, lactam, imide, acid anhydride or lactone; the drugs unstable in water or solvents, such as procaine, pilocarpine and aspirin; the acid labile drugs, such as hydrogen potassium adenine nucleotidase inhibitor; the drugs with special taste, such as acetaminophen; the drugs easily oxidized; the drugs with poor solubility, such as cyclosporin, nifedipine and nicardipine; the drugs which is difficult to be absorbed by human body. The drugs also include morphine; ascorbic acid and captopril. The most preferred embodiment of the invention is acid labile drugs, in particular omeprazole.

The preparation according to the invention further comprises an alkaline salt of a drug, which is an inorganic and an organic salt such as carbonate, phosphate and citrate, formed by the drug in combination with an ion such as sodium, potassium, magnesium and calcium ion.

The term "oily compound" as used herein refers to the oils and fats useful for preparation of pharmaceuticals, such as mineral oil, paraffin, sesame oil, sunflower oil, olive oil, hydrogenated vegetable oil and lanolin or the mixture thereof. According to the invention, the alkaline salts of the oily compounds can also be used, which are the salts formed with alkaline compounds. The alkaline compounds include, such as, ammonium, sodium, potassium, magnesium, aluminum and calcium.

The term "enteric coating" as used herein refers to a coating which is soluble in enteric tracts, which is made from the material selected from the group consisting of: (1) polymers with carbohydrates such as cellulose acetate phthalate (CAP), cellulose acetate succinate, cellulose hydrogen phthalate, cellulose acetate trimellitate (CAT), hydroxypropyl methylcellulose phthalate (HP or HPMCP), hydroxypropyl methylcellulose acetate succinate (Aquot or HPMACAS), carboxymethyl ethylcellulose (CMEC), starch acetate phthalate and amylose acetate phthalate; (2) polymers with polyvinyl such as polyvinyl acetate phthalate (PVAP), polyvinyl acetate phthalate, styrene-maleic acid copolymer, methylacrylate-methacrylic acid copolymer (MPM-05), methylacrylate-methacrylic acid-methylmethacrylate copolymer (MPM-06) and methyl methacrylate-methacrylic acid copolymer (Eudragit L, S, L30D); and (3) shellac. The enteric acid is preferably the mixture of hydroxypropyl methylcellulose phthalate and acetate phthalate cellulose, methyl methacrylate-methacrylic acid copolymer or polyvinyl acetate phthalate. Said enteric coating optionally comprise a plasticizer.

The term "excipient" as used herein refers to any excipient suitable for mixing the used oily compound and drug. Said excipient is selected from the group consisting of starch, modified starch (such as carboxymethyl starch sodium), and cellulose (such as hydroxypropyl methylcellulose and carboxymethyl cellulose sodium).

The term "emulsifier" as used herein refers to a composition of $C_{6-18}$ organic fatty acid and an organic amine, or a polycarbon alcohol, or the mixture thereof. The $C_{6-18}$ organic fatty acid can be a saturated or unsaturated fatty acid or a fatty acid with multiple functional groups. The organic amine can be an organic amine with single functional group or multiple functional groups. Preferably, the organic amine is an alcohol amine. According to one preferred embodiment of the invention, the organic fatty acid is preferably a stearic acid and the organic amine is preferably an ethanolamine, diethanolamine or triethanolamine.

The term "polycarbon alcohol" refers to an alcohol with multiple carbons. According to one preferred embodiment of the invention, the polycarbon alcohol is cetyl alcohol.

The term "emulsified fluid" refers to a mixture formed by mixing oil compounds or the basic salts thereof and an emulsifier.

The term "emulsified suspension" refers to a mixture comprised of a drug or the alkaline salt thereof and an emulsified fluid.

The oral preparation of the invention can further comprise an alkaline compound. Said alkaline compound is selected from the group consisting of an oxide, hydroxide, carbonate, phosphate and citrate having one or more ammonium, sodium, potassium, magnesium, aluminum and calcium. Preferably, the alkaline compounds combine the alkaline salts of drugs to form alkaline granules.

According to the invention, a dispersant or suspension-assistant agent can be optionally added in the oral capsule preparation to facilitate the absorption and retain a long-term constancy. When the capsule encounters the intestinal fluid, the dispersant can disperse the oil drops in a very short time to increase the surface area for absorption and thus to facilitate the absorption of drugs. According to the invention, the dispersant, which can be an excipient, is a substance for facilitating the dispersion of the oil drops. The suspension-assisting agent can be any of the pharmaceutical acceptable agents which help the drug mixtures in the preparation of the invention to form a non-Newtonian fluid, i.e. a semisolid form. Therefore, the drugs are difficult to be precipitated and thus a long-term constancy is obtained.

The oral capsule preparation of the invention is a capsule coated with enteric coatings. According to the invention, the inner phase of the capsule preparation is a liquid or semi-solid wherein the drug particles or basic particles formed with basic compounds are suspended in the emulsified fluid formed by oil compounds and emulsifiers. Accordingly, after the capsule of the oral preparation of the invention dissolves in the enteric tract, the drugs therein can be dispensed and emulsified quickly by the emulsifier and the optionally added suspension-assisting agent and dispersant. Therefore, the drugs can be absorbed quickly and the degradation will be delayed.

The invention further provides a method of preparing the oral preparations of the invention, which comprises the steps of suspending a drug or the basic salts thereof in an emulsified fluid formed by mixing oil compounds or the basic salts thereof and an emulsifier, filling a capsule with the suspension, coating the outer surface of the capsule with an enteric coating.

According to one embodiment of the invention, the present method can further comprise the step of mixing the oil compounds and an emulsifier with an optionally added excipient, suspension-assisting agent and dispersant.

According to another embodiment of the invention, the method of preparing an oral capsule preparation of omeprazole comprises the steps of suspending omeprazole particles in an emulsified fluid formed by mixing oil compounds (or the salts thereof) and an emulsifier or an optionally added excipient, filling a capsule with the suspension, capping the capsule tightly and coating the capsule with an enteric coating. The method optionally comprises the steps of applying oil in the inner surface of the capsule and filling the oiled capsule with omeprazole. The enteric coating of the invention comprises hydroxypropyl methylcellolose phthalate, acetate phthalate cellulose, methyl methacrylate-methacrylic acid copolymer or polyvinyl acetate phthalate and an optional plasticizer.

According to the invention, any one of the conventional methods can be used to coat a capsule with an enteric coating. Preferably, the coating method includes immersion, sugar pan, fluid-bed and centrifugation.

The oral capsule preparation provided by the invention can keep the drugs therein away from those factors which make the drugs unstable, and facilitate the absorption of the drugs in the intestine. In addition, the preparation of the invention has many advantages, such as easy and simple preparing it, and providing excellent efficacy and stability.

The following examples are provided to further describe the invention. The examples are only used to illustrate but not to limit the invention.

EXAMPLES

Example 1

Tests for the Performance and Acid Resistance of Enteric Coating

The test compound and lactose were mixed well and the capsule No. 3 was filled with the mixture. The filled capsule was then sealed with gelatin and coated with enteric coating. The following test was conducted to measure the coating performance and the acid resistance of the enteric coatings formulated according to Table 1:

TABLE 1

Enteric Coating Formulations (g)

| | I | II | III | IV | V | VI |
|---|---|---|---|---|---|---|
| HPMCP | 60 | 60 | | | | |
| HPMCAS | | | 60 | | | |
| OPADRY OY-A | | | | 60 | | |
| Eudragit L30D | | | | | 200 | 875 |
| TEC | | | 12 | | | 45 |
| DBS | 9 | | | | | |
| PEG6000 | | | | | 9 | |
| Myvacet | | 9 | | | | |
| Talc | | | | | 20 | |
| SAPN80 | | | | 0.0156 | 0.015 | |
| Ethanol | 336 | 336 | | | | |
| Diclromethane | 336 | 336 | | | | |
| Water | | | 660 | 420 | 520 | 325 |
| 30% Ammonia solution | | | | | 2.4 | |

HPMCP: hydroxypropyl methylcellulose phthalate

HCMCAS: hydroxypropyl methylcellulose acetate succinate

OPADRY OY-A (the product name of COLORCON ®)

Eudragit L30D (product name)

TEC: triethylcitrate

DBS: dibutylsebacate

Myvacet® (product name)

A coating solution was produced by the above formulations, respectively. 600 g of sealed capsules was put in a coating pan. The polymer solution was then sprayed onto the capsules. The capsules were dried to water content below 2% and put in a sealed container. Six of each group of the resulting capsules were analyzed in an enteric test. The enteric test was conducted according to USP XXIII Enteric coated dissolution method B. The capsules were maintained in a spiral hollow system made of stainless wire at the water-bath temperature of 37±0.5° C. and the rotation rate of 50 rpm to avoid the capsules float out of the water surface. The dissolution test has two stages. At the first stage, the capsules were dissolved in 1000 ml of 0.1 N hydrochloric acid for two hours. Then, the hydrochloric acid was dried out and 1000 ml phosphate buffer of pH 6.8 was added to continue the second stage. The second stage was to measure the acid resistance of the enteric coatings. The capsules were filled with a suitable test compound in place of omeprazole. The filled capsules were then coated with various enteric coating formulations and dissolved in 0.1 N hydrochloric acid. The amount of the released compound was analyzed with UV light to measure the acid resistance of the enteric coated capsules. The result of the dissolution test as shown in Table 2 indicates that the enteric coated capsules have excellent acid resistance.

TABLE 2

Data of acid resistance from the enteric coated dissolution test

| | Formulation | | | | |
|---|---|---|---|---|---|
| | I | II | III | IV | V |
| Dissolution time | Drugs dissolution % | | | | |
| 1 hour | 0.00 | 0.00 | 0.00 | 0.00 | 0.00 |
| 2 hours | 0.00 | 0.03 | 0.01 | 0.00 | 0.00 |
| 3 hours | 0.00 | 0.27 | 0.29 | 0.00 | 0.00 |
| 4 hours | 0.04 | 0.33 | 1.16 | 0.00 | 0.03 |
| 5 hours | 0.12 | 0.49 | 2.73 | 0.15 | 0.06 |
| 6 hours | 0.18 | 0.67 | 4.41 | 0.21 | 0.14 |

Example 2

The Formulations of the Capsule Preparation of the Invention

1. Formulation A

The mineral oil, stearic acid and ethanolamine were heated and mixed to form an emulsified fluid. Omeprazole was added to the resulting emulsified fluid and mixed well by a homogenizer to obtain Formulation A in the form of an emulsified suspension.

| Formulation A | |
|---|---|
| Mineral oil | 360.0 g |
| Omeprazole | 40.0 g |
| Stearic acid | 78.6 g |
| Ethanolamine | 21.4 g |

2. Formulations B and C

The mineral oil, stearic acid and triethanolamine were heated and mixed to form an emulsified fluid. Omeprazole was added to the resulting emulsified fluid and mixed well by a homogenizer to obtain Formulation B in the form of an emulsified suspension.

| Formulation B | |
|---|---|
| Mineral oil | 410.0 g |
| Omeprazole | 40.0 g |
| Stearic acid | 30.0 g |
| Triethanolamine | 20.0 g |

600 g of Formulation B was taken to prepare Formulation C in the form of enteric coating capsules using the formulation V and method as described in example 1.

3. Formulation D

The paraffin, stearic acid and ethanolamine were heated and mixed to form an emulsified fluid. Omeprazole was added to the resulting emulsified fluid and mixed well by a homogenizer to obtain Formulation D in the form of an emulsified suspension.

| Formulation D | |
| --- | --- |
| Paraffin | 360.0 g |
| Omeprazole | 40.0 g |
| Stearic acid | 78.6 g |
| Ethanolamine | 21.4 g |

4. Formulation E

The mineral oil, stearic acid, ethanolamine and cetyl alcohol were heated and mixed to form an emulsified fluid. Omeprazole was added to the resulting emulsified fluid and mixed well by a homogenizer to form an emulsified suspension. The emulsified suspension has the property of non-Newton fluid, which is a semisolid without separate layers in stationary state and returns to being fluid via stirring and shaking. Capsules were then filled with the emulsified suspension and sealed with gelatin to obtain Formulation E.

| Formulation E | |
| --- | --- |
| Mineral oil | 310.0 g |
| Omeprazole | 40.0 g |
| Stearic acid | 77.0 g |
| Ethanolamine | 23.0 g |
| Cetyl alcohol | 50.0 g |

5. Formulation F

The mineral oil, stearic acid, ethanolamine and cetyl alcohol were heated and mixed to form an emulsified fluid. Omeprazole was added to the resulting emulsified fluid and mixed well by a homogenizer. Carboxymethyl cellulose sodium (Primojel®) was added to increase the viscosity of the emulsified fluid. Finally, Formulation F was obtained.

| Formulation F | |
| --- | --- |
| Mineral oil | 335.0 g |
| Omeprazole | 40.0 g |
| Stearic acid | 38.5 g |
| Ethanolamine | 11.5 g |
| Cetyl alcohol | 50.0 g |
| Carboxymethyl cellulose sodium (Primojel ®) | 25.0 g |

6. Formulations G and H

The mineral oil, stearic acid, ethanolamine and carboxymethyl cellulose sodium (Primojel®) were heated and mixed to form an emulsified fluid. Omeprazole was added to the resulting emulsified fluid and mixed well by a homogenizer to obtain Formulation G in the form of an emulsified suspension.

| Formulation G | |
| --- | --- |
| Mineral oil | 205.0 g |
| Omeprazole | 40.0 g |
| Stearic acid | 38.5 g |
| Ethanolamine | 11.5 g |
| Carboxymethyl cellulose sodium (Primojel ®) | 205.0 g |

600 g of Formulation G was taken to prepare Formulation H in the form of enteric coating capsules using the Formulation II and method as described in example 1.

7. Formulations I and J

The mineral oil, stearic acid and ethanolamine were heated and mixed to form an emulsified fluid. Omeprazole was added to the resulting emulsified fluid and mixed well by a homogenizer to obtain Formulation I in the form of an emulsified suspension.

| Formulation I | |
| --- | --- |
| Mineral oil | 435.0 g |
| Omeprazole | 40.0 g |
| Stearic acid | 17.0 g |
| Diethanolamine | 8.0 g |

600 g of Formulation I was taken to prepare Formulation J in the form of enteric coating capsules using the Formulation II and method as described in example 1.

8. Formulations K and L

Omeprazole was added to an emulsified fluid formed by heating and mixing mineral oil, stearic acid, ethanolamine and cetyl alcohol, and mixed well by a homogenizer to form an emulsified suspension. Capsules were filled with the emulsified suspension and sealed with gelatin. Finally, Formulation K was obtained in the form of an emulsified suspension.

| Formulation K | |
| --- | --- |
| Mineral oil | 360.0 g |
| Omeprazole | 40.0 g |
| Stearic acid | 68.2 g |
| Diethanolamine | 31.8 g |

600 g of Formulation K was taken to prepare Formulation L in the form of enteric coating capsules using the Formulation II and method as described in example 1.

9. Formulations M and N

The mineral oil, cetyl alcohol and carboxymethyl cellulose sodium (Primojel®) were heated and mixed to form an emulsified fluid. Omeprazole was added to the resulting emulsified fluid and mixed well by a homogenizer to obtain Formulation I in the form of an emulsified suspension.

| Formulation M | |
| --- | --- |
| Mineral oil | 205.0 g |
| Omeprazole | 40.0 g |
| Cetyl alcohol | 50.0 g |
| [Promojel] (Primojel ®) | 205.0 g |

600 g of Formulation M was taken to prepare Formulation N in the form of enteric coating capsules using the Formulation II and method as described in example 1.

10. Formulation O

The mineral oil, stearic acid, ethanolamine and cetyl alcohol were heated and mixed to form an emulsified fluid. Omeprazole was added to the resulting emulsified fluid and mixed well by a homogenizer. Carboxymethyl cellulose sodium (Primojel® R) was added to increase the viscosity of the emulsified fluid. Finally, Formulation O was obtained.

| Formulation O | |
|---|---|
| Mineral oil | 620.0 g |
| Omeprazole | 80.0 g |
| [Steric] Stearic acid | 77.0 g |
| 2-Aminoethanol | 23.0 g |
| Cetyl alcohol | 100.0 g |
| Carboxymethyl cellulose sodium [{](Primojel ® R) | 100.0 g. |

600 g of Formulation O was taken to prepare Formulation P in the form of enteric coated capsules using the Formulation VI and method as described in Example 1.

Example 3

The Comparison Between the Capsule Preparation of the Invention and the Preparation in Market The comparative dissolution test was carried out using Formulation L of Example 2 as described above and the preparation in market. The results show that the preparation of the invention has better dissolution in vitro than the preparation in market (see FIG. 2).

Example 4

Accelerated Stability Test

Accelerated stability test was carried out using Formulations G and I. Said accelerated stability test is used to detect the stability of a sample under the conditions of 40° C. and 75% relative humidity through the observation of the appearance and the measurement of the amount of the active ingredient. A sample stored under the above condition for six months is equivalent to that stored under room temperature for more than two years. It was found that the formulations of the invention retain an amount of the active ingredients of more than 95% after those formulations were tested in the stability test for eight months, indicating that the formulations of the invention have unexpectedly high stability.

Formulation O is also used in the accelerated stability test. The formulation O is stored at 25, 30 and 40° C. for six months respectively. The results as shown as below Table 3:

TABLE 3

| Temperature | Residual Amount of omeprazole Month | | | | |
|---|---|---|---|---|---|
| | 0 | 1 | 2 | 3 | 6 |
| 25° C. | 100.0 | 100.0 | 100.0 | 100.0 | 100.0 |
| 30° C. | 100.0 | 100.0 | 100.0 | 105.7 | 97.3 |
| 40° C. | 100.0 | 99.6 | 99.2 | 97.9 | 92.4 |

As shown in Table 3, the residual amount of omeprazole of the formulation O is higher than 90% under 25° C., 30° C. and 40° C. The preparation of the invention indeed has stability.

What is claimed is:

1. An oral capsule preparation, comprising:
a capsule comprising:
a substance selected from a group consisting of a drug and an alkaline salt thereof;
a substance selected from a group consisting of an oily compound and an alkaline salt thereof; and
an emulsifier; and
an enteric coating disposed on an outer layer of the capsule,
wherein said emulsifier comprises at least one substance from a group consisting of a $C_{6-18}$ organic fatty acid and an organic amine.

2. The oral capsule preparation of claim 1, wherein the drug comprises an acid labile drug.

3. The oral capsule preparation of claim 2, wherein the drug comprises omeprazole.

4. The oral capsule preparation of claim 1, wherein the alkaline salt of the drug comprises:
a plurality of inorganic ions selected from a group consisting of sodium ions, potassium ions, magnesium ions, and calcium ions, and
a plurality of organic salts selected from a group consisting of carbonate, phosphate and citrate.

5. The oral capsule preparation of claim 1, further comprising an excipient.

6. The oral capsule preparation of claim 1, wherein the oily compound comprises at least one substance selected from a group consisting of mineral oil, paraffin, sesame oil, sunflower oil, olive oil, hydrogenated vegetable oil, and lanolin.

7. The oral capsule preparation of claim 1, wherein the enteric coating comprises at least one material selected from a group consisting of carbohydrate polymers and polyvinyl polymers.

8. The oral capsule preparation of claim 7, wherein the enteric coating comprises a substance selected from a group consisting of cellulose acetate phthalate (CAP), cellulose acetate succinate, cellulose hydrogen phthalate, cellulose acetate trimellitate (CAT), hydroxypropyl methylcellulose phthalate (HP or HPMCP), hydroxypropyl methylcellulose acetate succinate (HPMACAS), carboxymethyl ethylcellulose (CMEC), starch acetate phthalate, amylose acetate phthalate, and shellac.

9. The oral capsule preparation of claim 8, wherein the enteric coating comprises a material selected from a group consisting of polyvinyl acetate phthalate (PVAP), styrene-maleic acid copolymer, methylacrylate-methacrylic acid copolymer (MPM-05), methylacrylate-methacrylic acid-methylmethacrylate copolymer (MAP-06), methyl methacrylate-methacrylic acid copolymer (Eudragit® L, S, L30D), hydroxypropyl methylcellulose phthalate, acetate phthalate cellulose, methyl methacrylate-methacrylic acid copolymer, and hydroxypropyl methylcellulose acetate succinate.

10. The oral capsule preparation of claim 7, wherein the enteric coating further comprises a plasticizer.

11. The oral capsule preparation of claim 1, further comprising at least one material selected from a group consisting of an alkaline compound, an excipient, a dispersant, and a suspension-assisting agent.

12. The oral capsule preparation of claim 11, wherein the alkaline salt of the drug comprises:
an ion selected from a group consisting of an oxide, a hydroxide, a carbonate, a phosphate, and a citrate; and
at least one ion selected from a group consisting of ammonium, sodium, potassium, magnesium, aluminum, and calcium.

13. The oral capsule preparation of claim 1, wherein the drug and the alkaline salt thereof form particles.

14. The oral capsule preparation of claim 5, wherein the excipient comprises a material selected from a group consisting of starch, modified starch, and cellulose.

15. The oral capsule preparation of claim 14, wherein the excipient comprises a material selected from a group consisting of carboxymethyl starch sodium, hydroxypropyl methylcellulose, and carboxymethyl cellulose sodium.

16. The oral capsule preparation of claim 1, wherein the $C_{6-18}$ organic fatty acid comprises a stearic acid.

17. The oral capsule preparation of claim 1, wherein the organic amine comprises an alcohol amine.

18. The oral capsule preparation of claim 1, wherein the organic amine comprises a material selected from a group consisting of ethanolamine, diethanolamine, and trietanolamine.

19. The oral capsule preparation of claim 1, wherein the emulsifier comprises:
    a stearic acid; and
    ethanolamine.

20. The oral capsule preparation of claim 1, wherein the emulsifier comprises:
    a stearic acid; and
    diethanolamine.

21. The oral capsule preparation of claim 1, wherein the emulsifier comprises:
    a stearic acid; and
    triethanolamine.

22. The oral capsule preparation of claim 1, wherein the emulsifier comprises:
    a stearic acid; and
    alcohol amine.

23. The oral capsule preparation of claim 22, wherein the alcohol amine comprises a material selected from a group consisting of ethanolamine, diethanolamine, and triethanolamine.

24. The oral capsule preparation of claim 1,
    wherein the prepared capsule preparation comprises a phase selected from a group consisting of a liquid and a semisolid, and
    wherein the drug and the alkaline salt thereof are suspended in an emulsified fluid comprising the oily compound and the emulsifier.

25. A method of preparing the oral capsule preparation of claim 1, comprising the steps of:
    suspending the substance selected from the group consisting of the drug and the alkaline salt thereof in an emulsified fluid formed by mixing oil compounds or the basic salts thereof and an emulsifier comprising the substance selected from the group consisting of the oily compound and the alkaline salt thereof and the emulsifier, thereby forming a suspension;
    filling the capsule with the suspension; and
    coating an outer surface of the capsule with the enteric coating,
    wherein said emulsifier comprises at least one substance selected from a group consisting of a $C_{6-18}$ organic fatty acid and an organic amine.

26. The method of claim 25, further comprising the steps of adding and mixing at least one material selected from a group consisting of an alkaline compound, an excipient, a dispersant, and a suspension-assisting agent.

27. The method of claim 25, further comprising the steps of:
    applying the oily compound and the emulsifier in an inner surface of the capsule, thereby forming an oiled capsule;
    filling the oiled capsule with the substance selected from the group consisting of the drug and the alkaline salt thereof; and
    capping the oiled capsule tightly.

28. The method of claim 25, wherein the coating step comprises a technique selected from a group consisting of immersing, sugar-panning, fluid-bedding, and centrifuging.

29. An omeprazole oral capsule preparation, comprising:
    a capsule comprising a substance selected from a group consisting of omeprazole and an alkaline salt thereof;
    a substance selected from a group consisting of an oily compound and an alkaline salt thereof; and
    an emulsifier; and
    an enteric coating disposed on an outer surface of the capsule,
    wherein said emulsifier comprises at least one substance selected from a group consisting of a $C_{6-18}$ organic fatty acid, an organic amine, and a polycarbon alcohol.

30. An omeprazole oral capsule preparation, comprising:
    a capsule comprising:
        a substance selected from a group consisting of omeprazole and an alkaline salt thereof;
        a substance selected from a group consisting of an oily compound and an alkaline salt thereof; and
        an emulsifier; and
    an enteric coating disposed on an outer surface of the capsule,
    wherein said emulsifier comprises:
        a stearic acid; and
        at least one organic amine selected from a group consisting of ethanolamine, diethanolamine, and triethanolamine.

31. An omeprazole oral capsule preparation, comprising:
    a capsule comprising a substance selected from a group consisting of omeprazole and an alkaline salt thereof;
    a substance selected from a group consisting of an oily compound and an alkaline salt thereof; and
    an emulsifier; and
    an enteric coating disposed on an outer surface of the capsule,
    wherein the emulsifier comprises cetyl alcohol.

32. An omeprazole oral capsule preparation, comprising:
    a capsule comprising:
        a substance selected from a group consisting of omeprazole and an alkaline salt thereof;
        a substance selected from a group consisting of an oily compound and an alkaline salt thereof; and
        an emulsifier; and
    an enteric coating disposed on an outer surface of the capsule,
    wherein the emulsifier comprises:
        cetyl alcohol;
        a stearic acid; and
        an organic amine selected from a group consisting of ethanolamine, diethanolamine and triethanolamine.

33. An omeprazole capsule preparation, comprising:
    a capsule comprising:
        omeprazole;
        a mineral oil; and
        an emulsifier; and
    an enteric coating disposed on an outer surface of the capsule, wherein the emulsifier comprises:
a stearic acid; and
an organic amine selected from a group consisting of ethanolamine, diethanolamine, and triethanolamine.

34. An omeprazole oral capsule preparation, comprising:
a capsule comprising:
omeprazole;
a mineral oil; and
an emulsifier; and
an enteric coating disposed on an outer surface of the capsule,
wherein the emulsifier comprises cetyl alcohol.

35. The oral capsule preparation of claim 2, wherein the alkaline salt of the drug comprises:
an ion selected from a group consisting of a carbonate, a phosphate, and a citrate; and
at least one ion selected from a group consisting of sodium, potassium, magnesium, and calcium.

36. The oral capsule preparation of claim 3, wherein the alkaline salt of the drug comprises:
an ion selected group consisting of a carbonate, a phosphate, and a citrate; and
at least one ion selected from a group consisting of sodium, potassium, magnesium, and calcium.

37. The oral capsule preparation of claim 8, wherein the enteric coating further comprises a plasticizer.

38. The oral capsule preparation of claim 9, wherein the enteric coating further comprises a plasticizer.

39. The oral capsule preparation of claim 12, wherein the drug and the alkaline salt thereof form particles.

40. The oral capsule preparation of claim 17, wherein the organic amine comprises an amine selected from a group consisting of ethanolamine, diethanolamine and triethanolamine.

41. The method of claim 26, wherein the coating step comprises a technique selected from a group consisting of immersing, sugar-panning, fluid-bedding, and centrifuging.

42. The method of claim 27, wherein the coating step comprises a technique selected from a group consisting of immersing, sugar-panning, fluid-bedding, and centrifuging.

* * * * *